United States Patent [19]

Bringhurst et al.

[11] Plant 4,487

[45] Nov. 20, 1979

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,815

[22] Filed: Oct. 23, 1978

[51] Int. Cl.[2] ..... A01H 5/03

[52] U.S. Cl. ..... Plt./49

[58] Field of Search ..... Plt./49, 48

*Primary Examiner*—Robert E. Bagwill

*Attorney, Agent, or Firm*—Townsend and Townsend

[57] ABSTRACT

A new and distinct variety of strawberry plant of a short-day type characterized by its good performance throughout California and its generally earlier production with exceptionally large, high quality fruit when winter planted in Coastal Southern California. The variety has a yield equal to or greater than the heavy yielding California cultivars Tigoa, Tufts and Aiko. Plants are vigorous and prolific runner makers, though runner generation is less than Tufts in fruit plantings. Fruit shape is medium long to long conic and much is flat wedged with a distinct small neck. Skin is smooth and glossy. Fruit averages larger in size than Tufts and its flavor is equal to or better than the best important California cultivars. Fruit is adequate for shipping and processing.

2 Drawing Figures

This invention relates to a new and distinctive short-day type strawberry cultivar designated C51 which is the result of a cross between "Tufts" (U.S. Plant Pat. No. 3,561) and Cal 64.57-108 (not patented).

C51 first fruited at the University of California, South Coast Field Station, Santa Ana in 1974 where it was selected and designated originally as Cal 72.266-604.

C51 has since been tested with favorable results and asexually reproduced by runners at various University of California field stations and facilities and has also been favorably tested in representative growers fields under strict control. Meristem originated virus negative stock for asexual reproduction is under development at the University of California.

FIG. 1 of the accompanying photographic color reproductions shows typical growth, flowering and fruiting characteristics of C51 in a winter planting in Southern California at mid-season.

Figure 1:
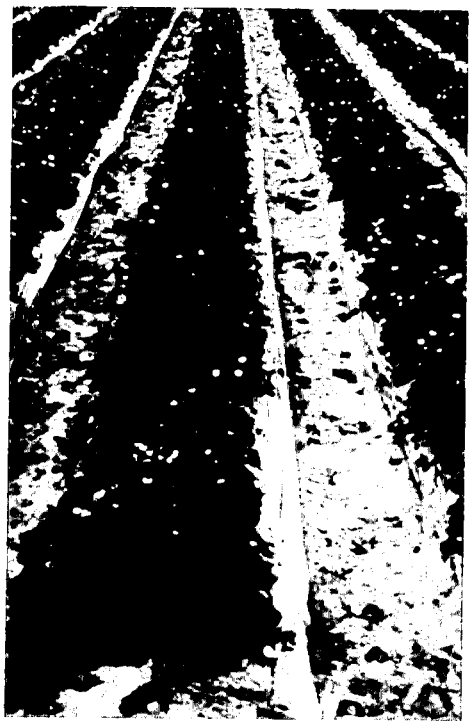
Figure 2:
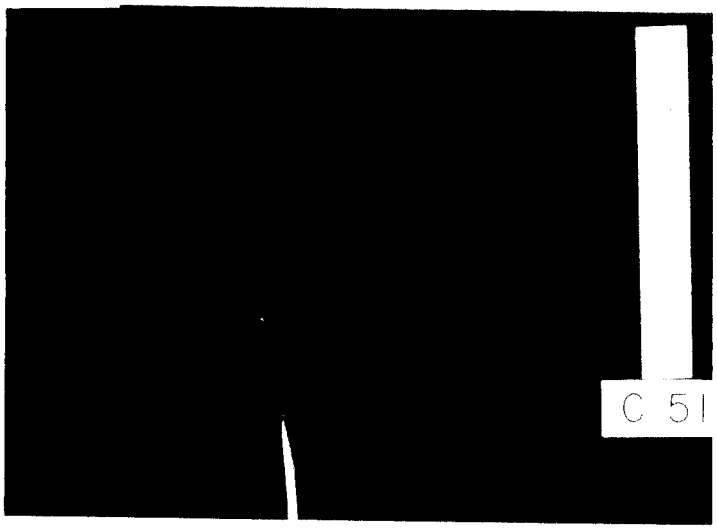
FIG. 2 shows a typical mid-summer mature leaf from a winter planted plant.
Figure 3:
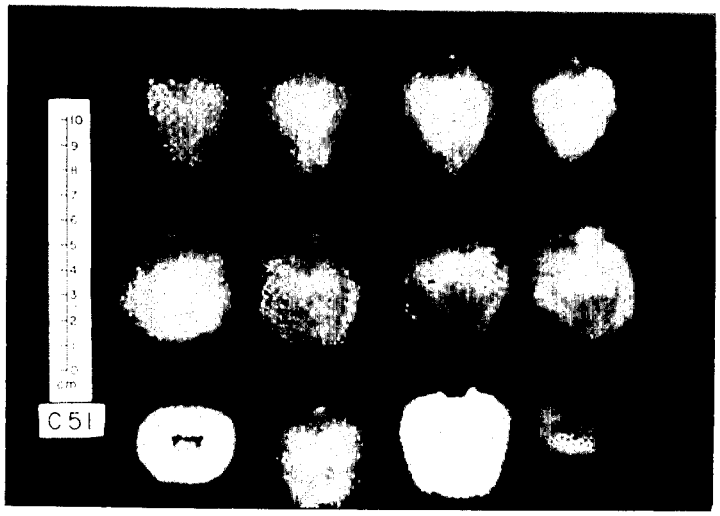
FIG. 3 shows representative mid-season fruit of C51 with longitudinal and cross section views.

C51 has performed well throughout California but has done best in winter plantings in coastal Southern California where it is generally earlier in production of exceptionally large, high quality fruit than any other California cultivar. Yield trials have demonstrated that it is likely to produce about as much or more fruit than the heavy yielding California cultivars "Tioga" (not patented), "Tufts" and "Aiko" (U.S. Plant Pat. No. 3,981) under favorable conditions in summer or winter plantings.

The distinctive characteristics of this new strawberry cultivar described in detail below were observed upon its discovery and/or through the test period.

DESCRIPTION

Plants and foliage: C51 plants are semi erect in growth habit similar to "Tufts", medium large in size about equal to "Tufts" or "Tioga" and much larger than "Aiko". Bract leaves occur on about 30% of the petioles of winter planted plants but seldom if ever on summer planted ones, much less than "Tioga", "Tufts" or "Aiko". Leaflets of C51 are about 15% larger than those of "Tioga" or "Tufts" and about 35% larger than those of "Aiko". They are distinctly lighter in color than those of "Tioga", "Tufts" or "Aiko"; about 2.5 GY 6/8 vs. 2.5 GY 4/3, 7.5 GY 5/7 and 7.5 GY 4.4, respectively (Munsell Color System — Nickerson Color Fan). The leaflets have about the same number of serrations as those of "Aiko" and "Tioga" (av of ±10/half blade) but less than "Tufts" (av of ±12/half blade) as averaged over the half blades of the 3 leaflets on mid-season mature leaves at Watsonville. The plants are vigorous and C51 is a prolific runner maker in the nursery. It generates less runners than "Tufts" in fruit plantings.

Isozymes in leaf extracts: Phosphoglucose isomerase (PGI): C51 gave a fast 3 banded pattern similar to that of "Cruz" (U.S. Plant Pat. No. 3,979) 35/35 35/35 35/35 35/40 mm, different than the "Tioga" single band; the "Tufts" slow 3 banded or the "Aiko" 5 band patterns (Scandalios. 1969. Biochem. Genet. 3:37–79).

Flowering and flowers: C51 is a standard short-day type that commences flowering earlier than "Tufts" or "Tioga" in winter plantings in coastal Southern California. Inflorescences are about as long as those of "Tufts", much longer than those of either "Aiko" or "Tioga". The flowers are highly self fertile with ample pollen throughout the season.

Fruit and Fruiting: C51 has medium long to long conic fruits almost always smooth, usually somewhat hollow centered and much of it is flatly wedged with a distinct small neck. The general shape and appearance of the fruit is very similar to that of "Tufts" but it appears to be less prone to roughness. The fruit skin color of C51 is distinctly redder than that of "Tufts", about 6 R 4/12 vs. 7.5 R 5.5/12, respectively (ibid). The finish is glossy and the flesh color is about the same as the skin, ranging to only slightly lighter in the center. The calyx is relatively small and distinctly reflexed. The achenes are slightly larger than those of "Tufts" and tend to be exserted similarly to those of "Tufts". The fruit is slightly less firm and less durable that that of "Aiko", "Tioga" or "Tufts", giving penetrometer readings of ±6.2 vs. ±6.7 for the three cultivars at Watsonville. The fruit has averaged somewhat larger in size than that of "Tufts" in most tests, typically about ±23 g/fr vs. ±21 for "Tufts".

Fruit quality—Ascorbic acid: C51 has averaged ±42 mg/100 g fresh fruit, slightly greater than "Tioga" (±40), slightly less than "Tufts" (±45) and considerably less than "Aiko" (±60) as tested by the method of Loeffler and Ponting. 1942. J. Indust. Eng. Chem. 14:846. Soluble solids: C51 averaged ±9.1%, not significantly different from "Aiko", "Tioga" or "Tufts" according to our tests or mid-summer Watsonville fruit.

The flavor of C51 is equal to or better than that of the best important California cultivars in our opinion. Many have judged it exceptionally good. As a shipping fruit, it is very adequate and it is promising for processing.

We claim:

1. The new and distinct variety of strawberry plant herein described and illustrated, and identified by the characteristics enumerated above.

* * * * *